(12) United States Patent
Pruter

(10) Patent No.: US 7,316,650 B1
(45) Date of Patent: *Jan. 8, 2008

(54) METHOD AND SYSTEM FOR SUPPORTING AN IMAGING TRANSCEIVER

(76) Inventor: Rick L Pruter, 21 Woodcrest La., NE., Iowa City, IA (US) 52240

( * ) Notice: Subject to any disclaimer, the term of this patent is extended or adjusted under 35 U.S.C. 154(b) by 684 days.

This patent is subject to a terminal disclaimer.

(21) Appl. No.: 10/248,490

(22) Filed: Jan. 23, 2003

Related U.S. Application Data

(63) Continuation-in-part of application No. 09/682,147, filed on Jul. 26, 2001, now Pat. No. 6,565,050.

(51) Int. Cl.
*A61B 8/00* (2006.01)
*F16M 13/00* (2006.01)

(52) U.S. Cl. .................... 600/437; 248/158

(58) Field of Classification Search .......... 600/437, 600/443–447, 459; 128/915, 916; 248/157–158, 248/161, 162.1, 176.3, 186.2, 187.1
See application file for complete search history.

(56) References Cited

U.S. PATENT DOCUMENTS

| | | | |
|---|---|---|---|
| 1,537,140 A | | 5/1925 | Russell et al. |
| 1,571,959 A | | 2/1926 | Mulligan |
| 3,475,075 A | | 10/1969 | Stone, Jr. |
| 3,777,740 A | * | 12/1973 | Hokanson .................. 600/455 |
| 3,891,301 A | | 6/1975 | Heller |
| 3,991,317 A | | 11/1976 | Kunne et al. |
| 4,052,888 A | * | 10/1977 | Brown et al. ................. 73/625 |
| 4,365,344 A | | 12/1982 | Dornheim |
| 4,548,373 A | | 10/1985 | Komura |
| 4,741,014 A | | 4/1988 | Lajus |
| 4,854,301 A | * | 8/1989 | Nakajima ................... 600/102 |
| 4,881,709 A | | 11/1989 | Nakamura |
| 4,894,855 A | | 1/1990 | Kresse |
| 5,023,899 A | | 6/1991 | Ohlson |
| 5,157,707 A | | 10/1992 | Ohlson |
| 5,348,014 A | * | 9/1994 | Okado ........................ 600/445 |
| 5,441,505 A | * | 8/1995 | Nakamura ................... 606/130 |
| 5,609,560 A | * | 3/1997 | Ichikawa et al. ........... 600/101 |
| 5,703,922 A | * | 12/1997 | Rattner ........................ 378/65 |
| 5,933,191 A | | 8/1999 | Ariga et al. |
| 6,110,112 A | * | 8/2000 | Heywang-Koebrunner . 600/439 |
| 6,178,225 B1 | | 1/2001 | Zur et al. |
| 6,183,415 B1 | | 2/2001 | Gartner |
| 6,409,735 B1 | * | 6/2002 | Andre et al. ................ 606/130 |
| 6,514,239 B2 | * | 2/2003 | Shimmura et al. ............. 606/1 |
| 6,565,050 B1 | * | 5/2003 | Pruter ........................ 248/158 |
| 6,665,554 B1 | * | 12/2003 | Charles et al. .............. 600/427 |
| 2001/0034530 A1 | | 10/2001 | Malackowski et al. | |

OTHER PUBLICATIONS

*Sure-Point, Stepping & Stabilizing Systems for Seed Implantation*, Amertek Medical, Inc., no date.
*RPT 600 Precision Stabilizer*, Radiaton Therapy Products, 1998.
*AccuSeed 3D Pro, The future of brachytherapy*, Tayman Medical, 1999.

* cited by examiner

*Primary Examiner*—Francis J. Jaworski
(74) *Attorney, Agent, or Firm*—Simmons Perrine PLC

(57) ABSTRACT

A system and method for supporting an ultrasound transducer or other medical device from a position above a patient support surface using an arched overhead boom and a tool balancer or multi-directional articulating extendable mount.

6 Claims, 1 Drawing Sheet

METHOD AND SYSTEM FOR SUPPORTING AN IMAGING TRANSCEIVER

CROSS REFERENCE TO RELATED APPLICATIONS

The present invention is a continuation-in-part application of and generally relates to co-pending U.S. patent application entitled "Method and System for Supporting An Imaging Transceiver" filed on Jul. 26, 2001, now U.S. Pat. No. 6,565,050, by the same inventor, and having application Ser. No. 09/682,147, which application is incorporated herein in its entirety by this reference.

BACKGROUND OF INVENTION

In recent years, handheld medical imaging transceivers, such as ultrasound and gamma ray transceivers, have been used extensively for various medical imaging situations. In certain situations, such as trans-rectal and trans-vaginal procedures, the imaging transceiver is coupled to a transceiver mount that is either floor or wall mounted or mounted to the bed or examination table. These transceiver mounts typically have some mechanism for stabilizing the transceiver from a point originating from the side of the patient or below the patient.

While these transceiver mounts have been used extensively in the past, they do have some drawbacks. First of all, the use of patient level and below support mechanisms often result in wires and other apparatus being placed on or in the near proximity of the patient. Increased contact of a transceiver wire with the patient increases the likelihood that distant movements of the patient (e.g., moving a leg with a wire draped over it), may result in unwanted motion of the transceiver. Secondly, these mounts are typically too cumbersome to be used regularly in certain applications like wide area, non-invasive scanning procedures, such as general fetal examinations. When the transceiver mounts are not used, their benefits are not realized.

It should also be noted that it is well known in the medical field to employ overhead lamps on adjustable booms over a patient.

Consequently, there exists a need for improved methods and systems for supporting a medical imaging transceiver in an efficient manner.

SUMMARY OF INVENTION

It is an object of the present invention to provide a system and method for stabilizing a medical imaging transceiver in an efficient manner.

It is a feature of the present invention to utilize an overhead support mechanism for a medical imaging transceiver.

It is another feature of the present invention to include a counter-balancing overhead medical imaging transceiver support.

It is another feature of the present invention to include a multi-directional jointed articulating overhead support arm for medical imaging transceivers.

It is another feature of the present invention to include a stabilizing mattress board.

It is another feature of the present invention to include a stabilizing bed clamp.

It is another feature of the present invention to include a rolling floor stand with locking wheels.

It is an advantage of the present invention to achieve improved efficiency in supporting medical imaging transceivers.

The present invention is an apparatus and method for supporting medical imaging transceivers, designed to satisfy the aforementioned needs, provide the previously stated objects, include the above-listed features, and achieve the already articulated advantages. The present invention is carried out in a "wasted time-less" manner in a sense that the time consumed with temporarily storing and retrieving the stored transceiver has been greatly reduced. Similarly, the present invention is a "fatigue-less" mount in the sense that the fatigue associated with holding a medical imaging transceiver can be reduced.

Accordingly, the present invention is a system and method including an overhead medical imaging transceiver support device which simultaneously provides support and an ability to maneuver and manipulate a transceiver without encroaching, with equipment and/or wires, into a zone, about the patient, defined at its upward extent by the lowest portion of the transceiver and at its lowest extent, a plane upon which the patient rests.

BRIEF DESCRIPTION OF DRAWINGS

The invention may be more fully understood by reading the following description of the preferred embodiments of the invention, in conjunction with the appended drawings wherein.

DETAILED DESCRIPTION

Figure 1:
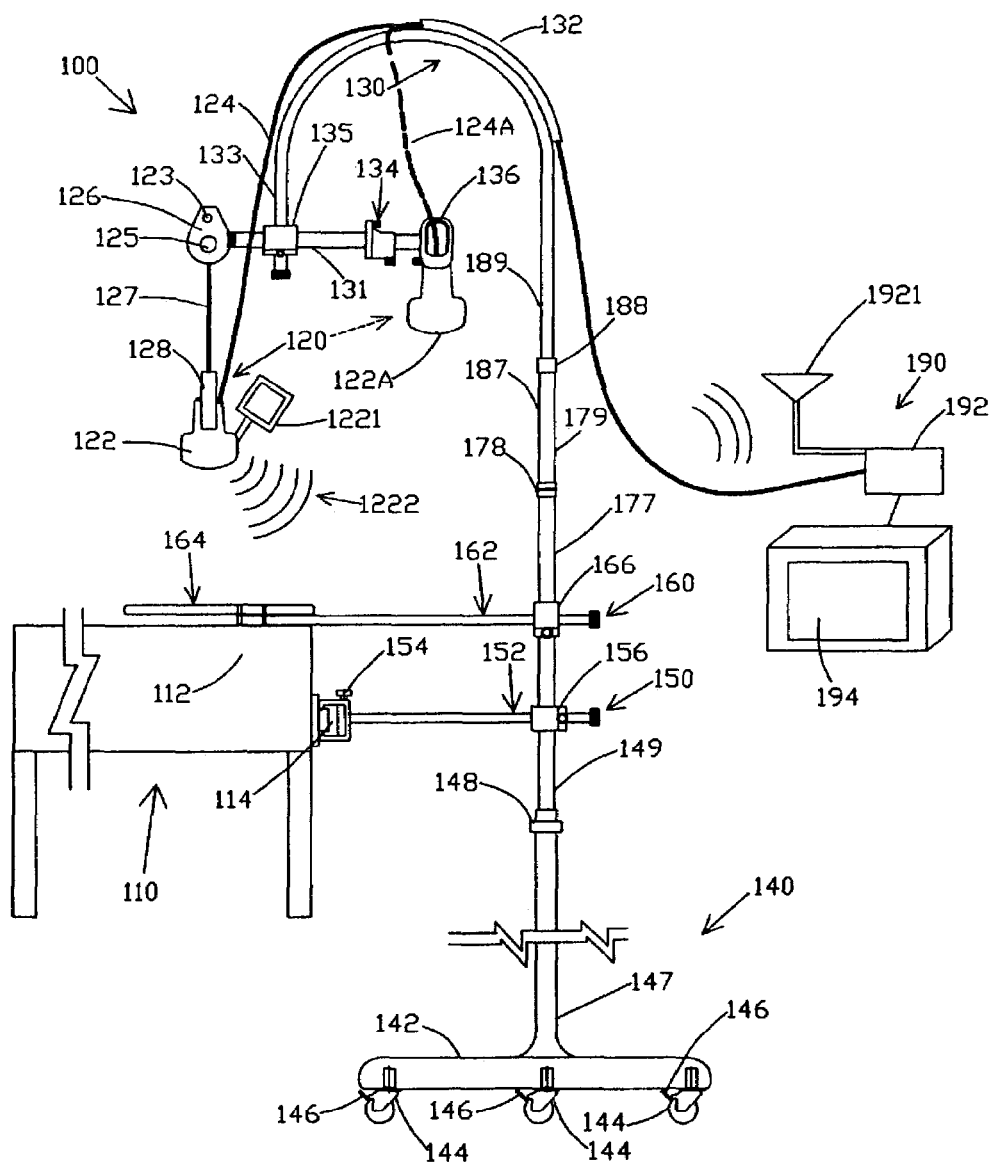
FIG. 1 is a side view of a system of the present invention.

Now referring to the drawings wherein like numerals refer to like matter throughout, and more specifically referring to FIG. 1, there is shown an overhead medical imaging transceiver support system of the present invention generally designated 100. Overhead medical imaging transceiver support system 100 includes an examination table, bed or other patient support device 110, which has a mattress, cushion or patient resting surface 112 thereon for supporting the patient above the floor. Overhead medical imaging transceiver support system 100 includes a medical imaging transceiver system terminal end 120, which includes a medical imaging transceiver 122. These transceivers are well known in the medical imaging field. They may include ultrasound transducers, gamma ray transceivers, or any other type of device which emits a signal and receives reflections therefrom and then provides a signal to a medical imaging system 190 for generating an image of a portion of a human body. The term "medical device" is used herein to include medical imaging transceivers, medical instruments, cryotherapy devices and other medical tools, but the term shall specifically exclude devices which are merely adjustable overhead lamps. It should be understood that the present invention is intended to include systems which substitute medical devices for the medical imaging transceivers described herein. Medical imaging transceiver power and signal cable 124 is used to connect medical imaging transceiver 122 with medical imaging system 190. Medical imaging transceiver power and signal cable 124 can provide power and signals in one or more lines. Medical imaging transceiver balancer 126 is a device which is used to support the weight of medical imaging transceiver 122. Medical imaging transceiver balancer 126 can be any type of device which is capable of maintaining an upward pressure on the medical imaging transceiver 122 so as to hold it in place once the physician or technician's hand is removed from the medical imaging transceiver 122 or the medical imaging transceiver adapter 128 which surround and supports and couples the medical imaging transceiver 122 with the medical imaging transceiver balancer support line 127. Medical imaging transceiver balancer 126 can be constructed like a tool balancer which are well known in the field of factory automation and ergonomic engineering. Medical imaging transceiver balancer 126 may have a tension adjuster 125 which is used to control the requisite force to pull medical imaging transceiver balancer support line 127 further out of medical imaging transceiver balancer 126. Tension adjuster 125 can be tuned to just hold the medical imaging transceiver 122 suspended. Medical imaging transceiver balancer 126 may also include a line actuator 123 which, if manipulated in a predetermined manner, causes the medical imaging transceiver balancer support line 127 to return without the need to make an adjustment to the tension adjuster. Line actuator 123 could also be configured, upon a different manipulation, to function as a lock on the medical imaging transceiver balancer support line 127, not allowing it to move in either direction. The details of the designs of medical imaging transceiver balancer 126 with line actuator 123, and tension adjuster 125 are believed to be sufficiently described, so that a person having ordinary skill in the art of prior art tool balancers, with the aid of this description, could make and use the same without undue experimentation.

Medical imaging transceiver adapter 128 may be any type of adapter and may be a universal adapter for coupling with various types of transceivers. Medical imaging transceiver adapter 128 may be a contoured clamshell-shaped clamp which has contours adapted and configured to fit to a commercially available medical imaging transceiver 122. The medical imaging transceiver adapter 128 has a screw actuated variable clamp force characteristic. Depending upon the weight of the medical imaging transceiver 122 actually used, the tension provided by medical imaging transceiver balancer 126 can be adjusted using tension adjuster 125.

Medical imaging transceiver 122 is shown coupled to medical imaging display and input device 194 via medical imaging transceiver and signal cable 124. However, it should be understood that medical imaging transceiver 122 could be coupled to medical imaging display and input device 194 via a wireless connection, such as via radio or IR Signals 1222 and an antenna 1921. In such cases, medical imaging transceiver 122 could be battery powered.

In another alternate embodiment, medical imaging transceiver 122 could be either battery or non-battery powered, but have a compact display 1221 disposed on medical imaging transceiver 122. In such case, no signal wire would be necessary.

Medical imaging transceiver system terminal end 120 is disposed on the arched overhead pivoting boom 130. Arched overhead pivoting boom 130 is preferably made of a rigid material, such as a stainless steel rod or any other suitable material and configuration. Preferably, arched overhead pivoting boom 130 can be pivoted around third twisting retraction control joint 188 or any other mechanism which would allow pivoting. Arched overhead pivoting boom 130 has coupled thereto a wire guide 132 which guides the medical imaging transceiver power and signal cable 124 as the arched overhead pivoting boom 130 is pivoted and translated up and down, as well as when the medical imaging transceiver 122 is moved in and out of the medical imaging transceiver balancer 126. Wire guide 132 can be a simple tube disposed on arched overhead pivoting boom 130, or it can be a series of loops, etc. If arched overhead pivoting boom 130 is hollow, medical imaging transceiver power and signal cable 124 can be made to run therein. Medical imaging transceiver power and signal cable 124 can run, as shown by dashed line 124A, to medical imaging transceiver 122, shown as 122A if it is disposed in non-dangling medical imaging transceiver adapter 136. Multi-axis articulating assembly 134 is coupled to non-dangling medical imaging transceiver adapter 136 to provide support in combination with arched overhead pivoting boom 130. Multi-axis articulating assembly 134 can be any type of multi-axis adjustable joint, including a ball-and-socket-type joint. Also shown is joint 135, which allows three degrees of freedom: 1) rotation around the vertical section 133 of arched overhead pivoting boom 130; 2) translation up and down on vertical section 133; and 3) horizontal translation along mini-boom 131.

The Figure shows non-dangling medical imaging transceiver adapter 136 and medical imaging transceiver adapter 128 as alternative adapters. They may be both mounted on arched overhead pivoting boom 130 at the same time, or they may be alternately mounted. Medical imaging transceiver power and signal cable 124 is shown as being alternately positionable between medical imaging transceiver adapter 128 and non-dangling medical imaging transceiver adapter 136, but it should be understood that a second independent medical imaging transceiver power and signal cable could be used to run from medical imaging system 190 to a second independent medical imaging transceiver (not shown). Medical imaging transceiver adapter 128 and non-dangling medical imaging transceiver adapter 136 are shown as being coupled and supported by arched overhead pivoting boom 130. It should be understood that these adapters could also be coupled to some other overhead support system, such as a ceiling-mounted support or a wall-mounted support mounted at an overhead location. The term "overhead" is used herein to refer to an elevated location at least 24 inches above the mattress, cushion or patient resting surface 112, but in a preferred embodiment, it refers to an elevated position above the head of a physician or other medical technician involved in the imaging procedure.

Arched overhead pivoting boom 130 is coupled to or is integrated with third internal extension pole segment 189, which is coupled through third twisting retraction control joint 188 to third hollow vertical upright support pole 187. Third hollow vertical upright support pole 187 is coupled to or is integrated with second internal extension pole segment 179, which is coupled through second twisting retraction control joint 178 to second hollow vertical upright support pole 177. Second hollow vertical upright support pole 177 is coupled to or is integral with first internal extension pole segment 149, which is coupled through first twisting retraction control joint 148 to first hollow vertical upright support pole 147.

Third internal extension pole segment 189, third twisting retraction control joint 188 and third hollow vertical upright support pole 187 are representative of any type of known telescopic support system which could be substituted. It is also possible that the arched overhead pivoting boom 130 is coupled to a non-telescopic support.

First hollow vertical upright support pole 147 is shown as a part of floor stand assembly 140, which contains floor stand framework 142, wheels 144 and wheel locks 146.

Overhead medical imaging transceiver support system 100 can also include a bed rail stabilizing system 150, which is used to stabilize the overhead medical imaging transceiver support system 100 by providing an anchor to an examination table, bed or other patient support device 110 through a bed rail or other structural member 114 coupled thereto. Bed rail stabilizing system 150 includes a bed rail stabilizing boom 152 which is coupled to first internal extension pole segment 149 via bed rail stabilizer boom to upright joint 156. Bed rail stabilizer boom to upright joint 156 is preferably capable of providing three degrees of freedom to bed rail clamp 154. First of all, bed rail stabilizer boom to upright joint 156 is capable of 1) being moved vertically along first internal extension pole segment 149; and 2) capable of having bed rail stabilizing boom 152 slid therethrough; and 3) is capable of rotation around an axis defined by first internal extension pole segment 149. Bed rail stabilizer boom to upright joint 156 can be a rigid 90-degree angle between bed rail stabilizing boom 152 and first internal extension pole segment 149 or any other angle. Bed rail stabilizer boom to upright joint 156 could also be an adjustable joint which allows the angle between bed rail stabilizing boom 152 and first internal extension pole segment 149 to be varied, depending upon the particular needs of the user. Bed rail or other structural member 114 is coupled to bed rail stabilizing boom 152 through a bed rail clamp 154. Like bed rail stabilizer boom to upright joint 156, bed rail clamp 154 can have a fixed angular relationship, or it can be angularly adjustable.

Patient platform stabilizing system 160 is provided to give additional stabilization, when necessary. Patient platform stabilizing system 160 includes a patient platform stabilizing boom 162 coupled through patient platform stabilizer boom to upright joint 166 to first internal extension pole segment 149. Patient platform stabilizer boom to upright joint 166 can be similar to bed rail stabilizer boom to upright joint 156. Patient platform stabilizing boom 162 is coupled to a patient platform 164, which is placed upon mattress, cushion or patient resting surface 112, and the patient either sits or lies thereon. The weight of the patient and the resulting friction and engagement with the mattress, cushion or patient resting surface 112, provides a quick and easy and bed type independent method of providing stabilization. The notion of using a paddle or platform underneath the patient to stabilize medical equipment has been known in the prior art. Similarly, it has been known in the prior art to have an ultrasound transceiver coupled to a bed to provide stabilization.

The overhead medical imaging transceiver support system 100 includes a medical imaging system 190, which can be any type of imaging system including but not limited to ultrasound, gamma ray, etc. Medical imaging system 190 includes medical imaging electronics 192 and medical imaging display and input device 194.

In operation, the apparatus and method of the present invention as described in FIG. 1, could function as follows:

a patient is situated on an examination table, bed or other patient support device 110;

a medical professional moves a medical imaging transceiver 122 from a top supported overhead position to a top supported lower position nearer the patient situated on examination table, bed or other patient support device 110;

an imaging procedure is done and the medical imaging transceiver 122 is released from the medical professional's hand;

the medical imaging transceiver 122 remains substantially at a constant elevation while it is not grasped by the medical professional;

the medical professional views an image on medical imaging display and input device 194;

the medical professional again grasps the medical imaging transceiver 122 and performs an imaging procedure.

The medical professional again releases grasp of the medical imaging transceiver 122 and then actuates line actuator 123 by pressing a button, thereby causing medical imaging transceiver balancer support line 127 to retract until line actuator 123 is released by releasing the button.

Medical imaging transceiver 122 is thereby caused to rise to an elevated position.

The medical professional then can swing the medical imaging transceiver 122 away from the patient by moving arched overhead pivoting boom 130, or by rolling overhead medical imaging transceiver support system 100 on wheels 144.

In an alternate method, a multi-axis articulating assembly 134 and non-dangling medical imaging transceiver adapter 136 are used to position and support the medical imaging transceiver 122.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well.

Throughout this document, references are made to "vertical" and "horizontal"; these terms are intended to mean "substantially vertical" and "substantially horizontal". Minor deviations from vertical and minor deviations from horizontal are intended to be included therein.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

The invention claimed is:

1. A system for top supporting a medical device from an elevated position comprising:
    a medical device of the type used for medical imaging;
    a medical device adapter, configured for coupling with said medical device;
    a patient physical support device;
    a vertically adjustable support structure disposed above said patient physical support device;
    the support structure coupled to said medical device adapter and further configured to maintain support from a first elevated position of said medical device adapter in a second elevated position without continuous human intervention, where said second elevated position is lower than said first elevated position;
    said support structure is configured to allow for repositioning of said medical device adapter to a third elevated position and for maintaining support, from said first elevated position of said medical device adapter in said third elevated position without continuous human intervention;
    wherein said medical device is a medical imaging transceiver;
    said medical device adapter is a medical imaging transceiver adapter;
    said support structure supports said medical imaging transceiver adapter in a suspended configuration, where said medical imaging transceiver adapter is suspended by a retractable, tension-adjustable support line from above;

wherein said patient physical support device is an examination table of a type which is configured to entirely support a patient in each of a reclined position and an intermediate position between said reclined position and a sitting position;

wherein said support structure is floor mounted;

wherein said support structure comprises an overhead pivoting boom having a first laterally extending section disposed above said medical imaging transceiver adapter and a first vertical section at least a portion of which is disposed below said patient supporting surface;

wherein said overhead pivoting boom pivots around an axis defined by said first vertical section;

wherein said first vertical section is telescopic;

further comprising a first stabilizer which cooperates with said patient physical support device to provide stabilization of said first vertical section;

wherein said first stabilizer is a patient platform stabilizing system comprising:

a patient platform stabilizing boom, coupled to said first vertical section with at least two degrees of freedom;

a patient platform coupled to said boom which is configured for engagement with said patient physical support device when at least a portion of a patient's weight is placed upon said patient platform, where said engagement results in a stabilizing effect upon said first laterally extending section; and further comprising a second stabilizer, which cooperates with said patient physical support device, where said second stabilizer comprises:

a bed rail stabilizing boom coupled to said first vertical section;

a bed rail clamp coupled to said bed rail stabilizing boom; and, a bed rail stabilizer boom to first vertical section joint.

2. A method of generating medical images comprising the steps of:

providing a medical imaging transceiver;

grasping the medical imaging transceiver at a first location and placing the medical imaging transceiver in a second location which is against a patient supported by an examination table;

displaying an image representative of echo signals received by said medical imaging transceiver;

raising said medical imaging transceiver to a third location above said second location and terminating the step of grasping said medical imaging transceiver;

supporting said medical imaging transceiver from above by an adjustable device which selectively maintains, without a need for continuous human intervention, said medical imaging transceiver at fixed but variable heights above said examination table which is of a type which is configured to support a patient in each of a reclined position and an intermediate position between said reclined position and a sitting position;

wherein said step of supporting said medical imaging transceiver utilizes a tool balancer; and wherein said step of supporting said medical imaging transceiver utilizes an overhead boom which is coupled to a patient stabilizing boom which is coupled to a patient stabilizing platform which is disposed between a patient and said examination table.

3. A method of claim 2 wherein said medical imaging system is coupled to a display for displaying images via a cable.

4. A method of claim 2 wherein said medical imaging transceiver is coupled to a display which is supported by said adjustable device.

5. An apparatus for top supporting a medical device from an elevated position comprising:

a medical device of the type used for medical imaging;

a medical device adapter, configured for coupling with said medical device;

a patient physical support device;

a vertically adjustable support structure disposed above said patient physical support device;

the support structure coupled to said medical device adapter and further configured to maintain support from a first elevated position of said medical device adapter in a second elevated position without continuous human intervention, where said second elevated position is lower than said first elevated position;

said support structure is configured to allow for repositioning of said medical device adapter to a third elevated position and for maintaining support, from said first elevated position of said medical device adapter in said third elevated position without continuous human intervention;

wherein said medical device is a medical imaging transceiver;

said medical device adapter is a medical imaging transceiver adapter;

said support structure supports said medical imaging transceiver adapter in a suspended configuration, where said medical imaging transceiver adapter is suspended by a retractable, tension-adjustable support line from above;

wherein said patient physical support device is an examination table of a type which is configured to entirely support a patient in each of a reclined position and an intermediate position between said reclined position and a sitting position;

further comprising a first stabilizer which cooperates with said patient physical support device to provide stabilization of said first vertical section;

wherein said first stabilizer is a patient platform stabilizing system comprising:

a patient platform stabilizing boom, coupled to said first vertical section with at least two degrees of freedom;

a patient platform coupled to said boom which is configured for engagement with said patient physical support device when at least a portion of a patient's weight is placed upon said patient platform, where said engagement results in a stabilizing effect upon said support structure.

6. A medical imaging system comprising:

a support structure, disposed above and coupled to a patient physical support device;

a medical imaging device;

said support structure is configured to support the medical imaging device;

said medical imaging device further comprising a medical imaging transceiver which transmits and receives signals to and from a mass of tissue;

said support structure being configured to provide support of said medical imaging device from above;

said support structure being configured to provide support from above, without a need for continuous human intervention, at variable heights above said patient physical support device, using a retractable, tension-adjustable tool balancer;

wherein said patient physical support device is a patient examination table of a type which is configured to support a patient in each of a reclined position and an intermediate position between said reclined position and a sitting position;

wherein said medical imaging transceiver transmits signals to a display device disposed remote from said medical imaging transceiver;

wherein said medical imaging transceiver communicates with said display device via a wireless communication connection; and wherein said support structure comprises a first vertical section and further comprising a first stabilizer which cooperates with said patient physical support device to provide stabilization of said first vertical section;

wherein said first stabilizer is a patient platform stabilizing system comprising:

a patient platform stabilizing boom, coupled to said first vertical section with at least two degrees of freedom; and a patient platform coupled to said boom which is configured for engagement with said patient physical support device when at least a portion of a patient's weight is placed upon said patient platform, where said engagement results in a stabilizing effect upon said support structure.

* * * * *